(12) United States Patent
Farida et al.

(10) Patent No.: US 10,577,320 B2
(45) Date of Patent: Mar. 3, 2020

(54) METHOD FOR PREPARING CIS-ALKOXY-SUBSTITUTED SPIROCYCLIC 1-H-PYRROLIDINE-2,4-DIONE DERIVATIVES

(71) Applicant: Bayer CropScience Aktiengesellschaft, Monheim am Rhein (DE)

(72) Inventors: Taraneh Farida, Pulheim-Geyen (DE); Martin Littmann, Leverkusen (DE); Rafael Warsitz, Essen (DE); Michael Esser, Leverkusen (DE); Albert Schnatterer, Leverkusen (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 16/098,138

(22) PCT Filed: Apr. 26, 2017

(86) PCT No.: PCT/EP2017/059885
§ 371 (c)(1),
(2) Date: Nov. 1, 2018

(87) PCT Pub. No.: WO2017/191001
PCT Pub. Date: Nov. 9, 2017

(65) Prior Publication Data
US 2019/0144385 A1    May 16, 2019

(30) Foreign Application Priority Data
May 4, 2016 (EP) ..................... 16168243

(51) Int. Cl.
C07D 201/08 (2006.01)
C07D 207/38 (2006.01)
C07D 201/02 (2006.01)

(52) U.S. Cl.
CPC ......... *C07D 207/38* (2013.01); *C07D 201/02* (2013.01); *C07D 201/08* (2013.01)

(58) Field of Classification Search
None
See application file for complete search history.

(56) References Cited

U.S. PATENT DOCUMENTS

| | | | |
|---|---|---|---|
| 6,114,374 | A | 9/2000 | Lieb et al. |
| 6,255,342 | B1 | 7/2001 | Lieb et al. |
| 6,359,151 | B2 | 3/2002 | Lieb et al. |
| 6,504,036 | B1 | 1/2003 | Lieb et al. |
| 6,596,873 | B1 | 7/2003 | Lieb et al. |
| 7,638,547 | B2 | 12/2009 | Himmler et al. |
| 7,897,803 | B2 | 3/2011 | Himmler et al. |
| 2002/0010204 | A1 | 1/2002 | Lieb et al. |
| 2007/0032539 | A1 | 2/2007 | Himmler et al. |
| 2008/0167188 | A1 | 7/2008 | Fischer et al. |
| 2010/0056598 | A1 | 3/2010 | Himmler et al. |

FOREIGN PATENT DOCUMENTS

| | | |
|---|---|---|
| WO | 9805638 A2 | 2/1998 |
| WO | 2004007448 A1 | 1/2004 |
| WO | 2006024411 A2 | 3/2006 |

OTHER PUBLICATIONS

International Search Report of International Patent Application No. PCT/EP2017/059885 dated Jun. 30, 2017.

*Primary Examiner* — Kamal A Saeed
(74) *Attorney, Agent, or Firm* — McBee Moore & Vanik IP, LLC

(57) ABSTRACT

The present invention relates to novel methods for preparing cis-alkoxy-substituted spirocyclic 1-H-pyrrolidine-2,4-dione derivatives and also to novel intermediates and starting compounds, which are passed through or used in the method according to the invention.

26 Claims, No Drawings

METHOD FOR PREPARING CIS-ALKOXY-SUBSTITUTED SPIROCYCLIC 1-H-PYRROLIDINE-2,4-DIONE DERIVATIVES

CROSS REFERENCE TO RELATED APPLICATIONS

This application is a National Stage entry of International Application No. PCT/EP2017/059885 filed 26 Apr. 2017, which claims priority to European Patent Application No. 16168243.0, filed 4 May 2016.

BACKGROUND

Field

Description of Related Art

The present invention relates to novel methods for preparing cis-alkoxy-substituted spirocyclic 1-H-pyrrolidine-2,4-dione derivatives and also to novel intermediates and starting compounds, which are passed through or used in the method according to the invention.

The multi-stage reaction of alkoxy-substituted spirocyclic 1-H-pyrrolidine-2,4-dione derivatives is known (WO 98/05638, WO 04/007448).

A disadvantage of the method to date is that intermediates have to be isolated. The isolation of intermediates renders the method technically very cumbersome and leads to losses of yield. Waste water results from the workup which can only be disposed of with difficulty.

SUMMARY

The object of the present invention consists of providing novel, economically and ecologically more viable methods for preparing compounds of the formula (I).

By the method according to the invention, surprisingly, cis-alkoxy-substituted spirocyclic 1-H-pyrrolidine-2,4-dione derivatives (compounds of the formula (I)) may be prepared in a simpler manner, in a one-pot process, without isolation of the intermediates, in relatively high purity and in better yields, starting from compounds of the formula (II). By using the one-pot method, the amount of base (acid binder) and the amount of waste water can also be reduced.

It has now been found that compounds of the formula (I)

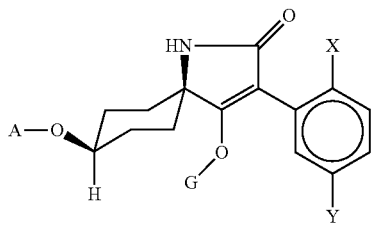

(I)

in which
X is $C_1$-$C_6$-alkyl, halogen, $C_1$-$C_6$-alkoxy, $C_1$-$C_6$-haloalkyl or $C_1$-$C_6$-haloalkoxy,
Y is hydrogen, $C_1$-$C_6$-alkyl, $C_1$-$C_6$-alkoxy, halogen, $C_1$-$C_6$-haloalkyl or $C_1$-$C_6$-haloalkoxy, wherein only one of the radicals X or Y may be $C_1$-$C_6$-haloalkyl or $C_1$-$C_6$-haloalkoxy,
A is $C_1$-$C_6$-alkyl,
G is the group

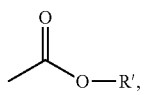

in which
R' is $C_1$-$C_{20}$-alkyl, $C_2$-$C_{20}$-alkenyl, $C_1$-$C_8$-alkoxy-$C_2$-$C_8$-alkyl or poly-$C_1$-$C_8$-alkoxy-$C_2$-$C_8$-alkyl, in each case optionally substituted by halogen,
is $C_3$-$C_8$-cycloalkyl optionally substituted by halogen, $C_1$-$C_6$-alkyl or $C_1$-$C_6$-alkoxy or
is phenyl or benzyl in each case optionally substituted by halogen, cyano, nitro, $C_1$-$C_6$-alkyl, $C_1$-$C_6$-alkoxy, $C_1$-$C_6$-haloalkyl or $C_1$-$C_6$-haloalkoxy,
are obtained
by firstly cyclizing compounds of the formula (II)

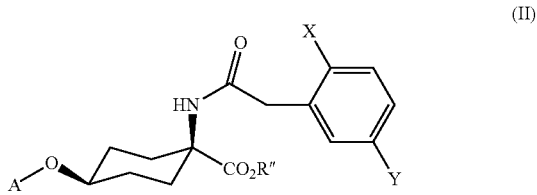

(II)

in which X, Y and A are as defined above and
R" is $C_1$-$C_6$-alkyl,
in the presence of a base and in the presence of solvents to give compounds of the formula (III)

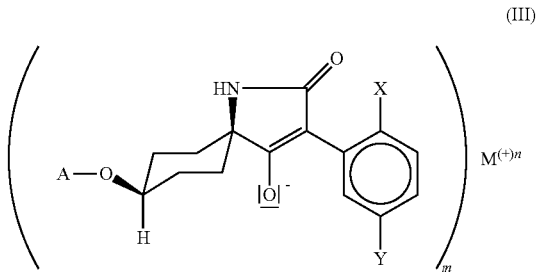

(III)

in which X, Y and A are as defined above and
M is an alkali metal ion, an ion equivalent of an alkaline earth metal, an ion equivalent of aluminium or an ion equivalent of a transition metal, or further
is an ammonium ion, in which optionally one, two, three or all four hydrogen atoms can be replaced by identical or different radicals from the groups $C_1$-$C_5$-alkyl, $C_1$-$C_5$-isoalkyl or $C_3$-$C_7$-cycloalkyl, which can in each case be substituted one or more times with fluorine, chlorine, bromine, cyano, hydroxy or be interrupted by one or more oxygen or sulphur atoms, or further
is a cyclic secondary or tertiary aliphatic or heteroaliphatic ammonium ion, for example morpholinium, thiomorpholinium, piperidinium, pyrrolidinium, or in each case protonated 1,4-diazabicyclo[2.2.2]octane (DABCO) or 1,5-diazabicyclo[4.3.0]undec-7-ene (DBU), or further
is a heterocyclic ammonium cation, for example in each case protonated pyridine, 2-methylpyridine, 3-methylpyridine, 4-methylpyridine, 2,4-dimethylpyridine, 2,5-dimethylpyridine, 2,6-dimethylpyridine, 5-ethyl-2-methylpyridine, pyrrole, imidazole, quinoline, quinoxaline, 1,2-dimethylimidazole, 1,3-dimethylimidazolium methyl sulphate, or further
is a sulphonium ion, or further
is a magnesium halogen cation,
m is the number 1, 2 or 3,
n is the number 1, 2 or 3.
and by reaction with compounds of the formula (IV)

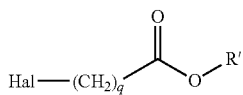
(IV)

in which
R' is $C_1$-$C_6$-alkyl,
q is the number 0 or 1,
and Hal represents halogen,
optionally in the presence of solvents and optionally in the presence of an acid binder and optionally in the presence of a phase transfer catalyst.

DETAILED DESCRIPTION OF A PREFERRED EMBODIMENT

In the abovementioned method, a redissociation of compounds of the formula (I) to compounds of the formula (III) can occur, which, by reaction with compounds of the formula (IV)

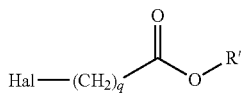
(IV)

in which R' and q are as defined above
and Hal represents halogen,
optionally in the presence of a solvent and optionally in the presence of an acid binder,
are recycled to give compounds of the formula (I) (recycling).

Moreover, the one-pot reaction can also be carried out in DMAC (dimethylacetamide)-free solvents, which represents a further method improvement, since the disposal of waste water containing DMAC is associated with high costs. In particular, this method is intended to be carried out with common solvents. It is possible to use toluene, xylene, alkanes such as n-hexane, n-heptane, n-octane, hydrocarbons such as pentane, hexane, heptane, cyclohexane, methylcyclohexane, benzene, halogenated hydrocarbons such as methylene chloride, chloroform, carbon tetrachloride, chlorobenzene, o-dichlorobenzene, dichloroethane. Preference is given to using toluene or xylene. Particular preference is given to using xylene.

In the formulae (I), (II), (III) and (IV)
X is preferably chlorine, bromine, methyl, ethyl, propyl, trifluoromethyl, methoxy, difluoromethoxy or trifluoromethoxy,
Y is preferably hydrogen, chlorine, bromine, methoxy, methyl, ethyl, propyl, trifluoromethyl or trifluoromethoxy, wherein only one of the radicals X or Y may be trifluoromethyl or trifluoromethoxy, A is preferably $C_1$-$C_6$-alkyl,
Hal is preferably chlorine, bromine, fluorine, iodine,
R' is preferably $C_1$-$C_6$-alkyl,
R" is preferably $C_1$-$C_6$-alkyl,
q is preferably the number 0 or 1,
X is particularly preferably chlorine, bromine, methyl, ethyl, methoxy, trifluoromethyl, trifluoromethoxy or difluoromethoxy,
Y is particularly preferably chlorine, bromine, methyl, ethyl, propyl, methoxy, trifluoromethyl or trifluoromethoxy, wherein only one of the radicals X or Y may be trifluoromethyl or trifluoromethoxy,
A is particularly preferably $C_1$-$C_4$-alkyl,
Hal is particularly preferably chlorine, bromine or fluorine,
R' is particularly preferably $C_1$-$C_4$-alkyl,
R" is particularly preferably $C_1$-$C_4$-alkyl,
q is particularly preferably the number 0 or 1,
X is especially preferably chlorine, bromine, methyl or trifluoromethyl, (particularly chlorine, bromine or methyl),
Y is especially preferably chlorine, bromine or methyl, (particularly methyl),
A is especially preferably methyl, ethyl, propyl, butyl or isobutyl, (particularly methyl or ethyl),
Hal is especially preferably chlorine or bromine,
R' is especially preferably methyl, ethyl, propyl, butyl or isobutyl,
R" is especially preferably methyl, ethyl, propyl, butyl or isobutyl,
q is especially preferably the number 0 or 1,
X is specifically methyl,
Y is specifically methyl,
A is specifically methyl,
Hal is specifically chlorine,
R' is specifically ethyl,
R" is specifically methyl,
q is specifically the number 0 or 1.
In the formula (III)
M is preferably lithium, sodium, potassium, caesium, magnesium, calcium or an ammonium ion, in which optionally one, two, three or all four hydrogen atoms can be replaced by identical or different radicals from the groups $C_1$-$C_5$-alkyl, $C_1$-$C_5$-isoalkyl or $C_3$-$C_7$-cycloalkyl, which can in each case be substituted one or more times with fluorine, chlorine, bromine, cyano, hydroxy, m is the number 1 or 2 and n is the number 1 or 2,
M is particularly preferably lithium, sodium, potassium, caesium, magnesium, calcium, m is the number 1 or 2 and n is the number 1 or 2,
M is especially preferably lithium, sodium, potassium, caesium, m is the number 1 and n is the number 1,
M is specifically sodium, m is the number 1 and n is the number 1.

Particular preference is given to the compound of the formula (I-1)

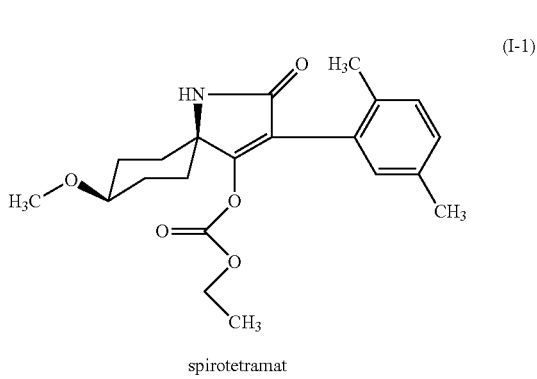

spirotetramat

Particular preference is given to the compound of the formula (II-1)

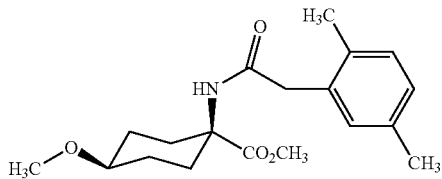

Particular preference is given to the compound of the formula (III-1)

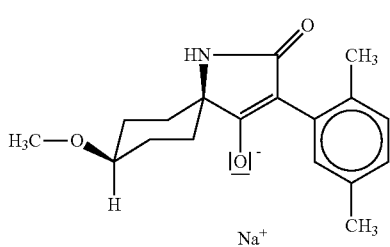

The above-listed general radical definitions and elucidations or those listed in preferred ranges may be combined arbitrarily with one another, in other words including combinations between the respective ranges and preferred ranges. They apply both to the end products and, correspondingly, to the precursors and intermediates.

In the definitions of the symbols given in the above formulae, collective terms which are generally representative of the following substituents were used:

Halogen: fluorine, chlorine, bromine and iodine

Alkyl: saturated straight-chain or branched hydrocarbyl radicals having 1 to 8 carbon atoms, for example $C_1$-$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl; heptyl, octyl.

Haloalkyl: straight-chain or branched alkyl groups having 1 to 8 carbon atoms, where in these groups some or all of the hydrogen atoms may be replaced, as mentioned above, by halogen atoms, for example $C_1$-$C_3$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and 1,1,1-trifluoroprop-2-yl.

The compounds of the formula (I) are known (WO 98/05638, WO 04/007448) or can be prepared by the methods described therein.

The compounds of the formula (II) are known (WO 98/05638, WO 04/007448, WO 13/144101) or can be prepared by the methods described therein.

The compounds of the formula (III) are novel and are the subject matter of the present invention.

The compounds of the formula (IV) are commercially available.

Scheme 1: One-Pot Reaction with Recycling

The course of the method according to the invention is represented by the following reaction scheme:

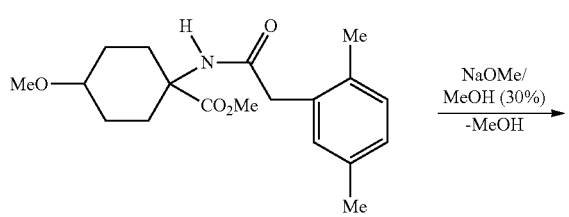

Compound of the formula (II-1) in DMAC

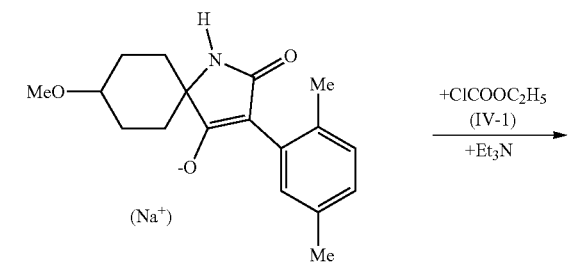

Compound of the formula (III-1)

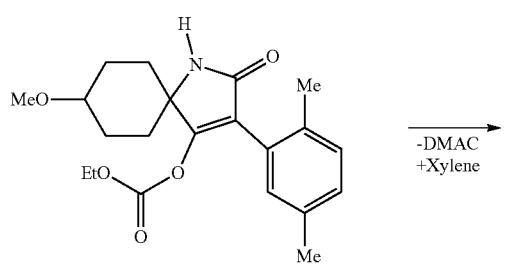

Compound of the formula (I-1) in DMAC

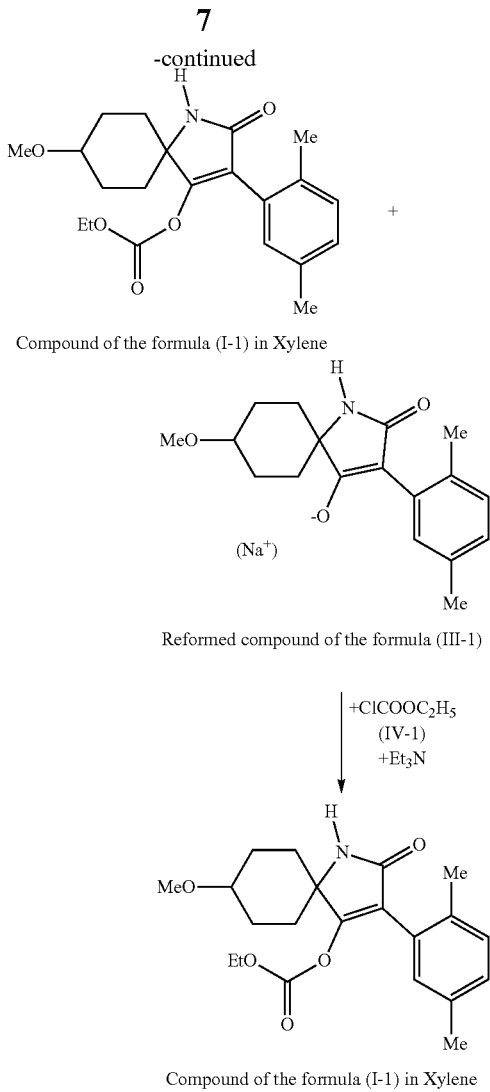

Owing to the cis/trans isomeric ratio of the compounds of the formula (II) which are used in the preparation method, the compounds of the formulae (I) and (III) are obtained in the form of cis/trans isomeric mixtures, wherein cis isomer is mainly formed in the method according to the invention.

The method is characterized in that compounds of the formula (II) having a high proportion of the cis isomer are cyclized to the corresponding compounds of the formula (III) in the presence of a base and in the presence of solvents. The compounds of the formula (III) are subsequently reacted with compounds of the formula (IV) to give compounds of the formula (I), optionally in the presence of solvents and optionally in the presence of an acid binder and optionally in the presence of a phase transfer catalyst.

The reaction temperature for preparing the compounds of the formula (III) may be varied in carrying out the method according to the invention. In general, temperatures between 20° C. and 110° C., preferably between 60° C. and 90° C., are employed.

Alkoxides may be used as base both as a solid and as a solution. For example, solid NaOMe or as a solution in methanol, solid NaOEt or NaOEt as a solution, sodium hydrogen carbonate, sodium or potassium hydroxide, alkaline earth metal hydroxides such as calcium hydroxide, alkali metal carbonates or alkoxides such as sodium or potassium carbonate, sodium or potassium tert-butoxide. In the bases mentioned, sodium can be replaced by potassium. Preference is given to solid sodium methoxide or 30% sodium methoxide in methanol. Particular preference is given to 30% sodium methoxide in methanol.

Solvents used can be DMAC, DMF, toluene, xylene, acetonitrile, alkanes such as n-hexane, n-heptane, n-octane, ethers such as diethyl ether, diisopropyl ether, dibutyl ether, anisole, methyl tert-butyl ether, methyl tert-amyl ether, glycol dimethyl ether, diglycol dimethyl ether, tetrahydrofuran or dioxane, ketones such as acetone, methyl ethyl ketone, methyl isopropyl ketone or methyl isobutyl ketone (MIBK), hydrocarbons such as pentane, hexane, heptane, cyclohexane, methylcyclohexane, benzene, halogenated hydrocarbons such as methylene chloride, chloroform, carbon tetrachloride, chlorobenzene, o-dichlorobenzene, dichloroethane, where polar solvents or a mixture of polar and non-polar solvents may be used as solvents. Preference is given to using DMAC, DMF, acetonitrile, ethers such as methyl tert-butyl ether, methyl tert-amyl ether, glycol dimethyl ether, diglycol dimethyl ether, tetrahydrofuran or dioxane, ketones such as acetone. Particular preference is given to using DMAC.

The reaction temperature for preparing the compounds of the formula (I) may be varied in carrying out the method according to the invention. In general, temperatures between 20° C. and 100° C., preferably between 50° C. and 70° C., are employed.

Solvents used can be DMAC, DMF, toluene, xylene, acetonitrile, alkanes such as n-hexane, n-heptane, n-octane, ethers such as diethyl ether, diisopropyl ether, dibutyl ether, anisole, methyl tert-butyl ether, methyl tert-amyl ether, glycol dimethyl ether, diglycol dimethyl ether, tetrahydrofuran or dioxane, ketones such as acetone, methyl ethyl ketone, methyl isopropyl ketone or methyl isobutyl ketone (MIBK), hydrocarbons such as pentane, hexane, heptane, cyclohexane, methylcyclohexane, benzene, halogenated hydrocarbons such as methylene chloride, chloroform, carbon tetrachloride, chlorobenzene, o-dichlorobenzene, dichloroethane, where polar solvents or a mixture of polar and non-polar solvents may be used as solvents. Preference is given to using DMAC, DMF, acetonitrile, ethers such as methyl tert-butyl ether, methyl tert-amyl ether, glycol dimethyl ether, diglycol dimethyl ether, tetrahydrofuran or dioxane, ketones such as acetone. Particular preference is given to using DMAC.

Useful as acid binders are all customary acid acceptors. The following can preferably be used: tertiary amines such as triethylamine, dimethylbenzylamine, pyridine, diazabicyclooctane (DABCO), diazabicycloundecene (DBU), diazabicyclononene (DBN), Hünig base and N,N-dimethylaniline, furthermore alkaline earth metal oxides such as magnesium oxide and calcium oxide, moreover alkali metal carbonates and alkaline earth metal carbonates such as sodium carbonate, potassium carbonate and calcium carbonate, and alkali metal hydroxides such as sodium hydroxide and potassium hydroxide, also sodium hydrogen carbonate. Preference is given to using triethylamine. Preference is also given to using dimethylbenzylamine.

Phase transfer catalysts used may be Aliquat 336, quaternary ammonium salts such as triethylbenzylammonium chloride, tetrabutylammonium bromide, Adogen 464 (methyltrialkyl ($C_8$-$C_{10}$)ammonium chloride) or TDA 1 (tris(methoxyethoxyethyl)amine) and also quaternary phosphonium salts such as tetrabutylphosphonium bromide. Preference is given to using Aliquat 336.

When carrying out the method according to the invention, the reaction components of the formula (II) are generally used in equimolar to about double equimolar amounts.

In a preferred method, the compounds of the formula (II) are reacted with NaOCH$_3$ (solid or as a solution in methanol) in DMAC to give the sodium salt of the compounds of the formula (III). The resulting methanol must be distilled off to avoid secondary components in the subsequent stage. The subsequent reaction with the acid chloride of the formula (IV) then takes place under catalytic acid binder addition (e.g. triethylamine). Subsequently, the solvent can be virtually completely distilled off under reduced pressure. Depending on the distillation conditions, compounds of the formula (I) may redissociate to compounds of the formula (III).

In an especially preferred method, after the solvent distillation, a small amount of acid binder (e.g. triethylamine) is added to the bottoms and with the acid chloride of the formula (IV) is recycled to give compounds of the formula (I). Using this method variant, virtually quantitative yields of compounds of the formula (I) are achieved (>95%) starting from compounds of the formula (II).

The reaction of compounds of the formula (II) in the presence of a base and in the presence of solvents to give compounds of the formula (III) and subsequent reaction with compounds of the formula (IV), optionally in the presence of solvents and optionally in the presence of an acid binder and optionally in the presence of a phase transfer catalyst, to give compounds of the formula (I) may be carried out, surprisingly, also in non-polar solvents (such as toluene, xylene, alkanes such as n-hexane, n-heptane, n-octane, hydrocarbons such as pentane, hexane, heptane, cyclohexane, methylcyclohexane, benzene, halogenated hydrocarbons such as methylene chloride, chloroform, carbon tetrachloride, chlorobenzene, o-dichlorobenzene, dichloroethane; preference is given to using toluene or xylene and particular preference is given to using xylene), if the reaction of compounds of the formula (III) with compounds of the formula (IV) is carried out in the presence of water. In this case, in the acylation stage (reaction with compounds of the formula (IV)) a suitable pH (preferably between pH 3 and 12, particularly preferably between pH 8 and 10) should be observed, in which the reactivity of the compounds of the formula (III) is still sufficiently high, but at the same time the stability of the product of the formula (I) and of the acid chloride of the compounds of the formula (IV) remains protected against alkaline saponification. The pH can be adjusted, for example, by continuous addition of a base (e.g. MOH or M(OH)$_2$ or M(OH)$_3$, where M is as defined above). Preference is given to aqueous sodium hydroxide solution. The reaction can be assisted by addition of catalytic amounts of a phase transfer catalyst. In a preferred method variant, the acid binder can be completely or partially replaced by a phase transfer catalyst. The reaction of the compounds of the formula (II) to give compounds of the formula (III) can be assisted by the addition of cosolvents. Alcohols such as methanol or ethanol may be used as cosolvent, preference being given to using methanol.

PREPARATION EXAMPLES

Example 1: One-Pot Method in DMAC (without Recycling after the DMAC Distillation) for Preparing the Compound of the Formula (I-1)

807.69 g of a solution of the compound of the formula (II-1) (0.81 mol) are initially charged in DMAC. At an internal temperature of 60-65° C., 159.04 g of a 30% sodium methoxide solution in methanol (0.88 mol) are metered in over ca. 2.5 h. Subsequently, methanol is distilled off under reduced pressure. The reaction solution is cooled to 50° C. and 9.62 g of triethylamine are metered in. Subsequently, 101.54 g of ethyl chloroformate (0.94 mol) are metered in between 52 and 56° C. over ca. 2.5 hours. The mixture is then further stirred for half an hour, then a portion of the DMAC is distilled off.

Subsequently, the residual DMAC is completely distilled off.

After addition of 403.85 g of xylene, the reactor content is cooled to 56° C.

Subsequently, the xylene solution is heated to ca. 80° C. and 173.08 g of a 1.6% sodium hydrogen carbonate solution are added and the aqueous phase separated. Subsequently, the mixture is then washed twice with 107.69 g of water each time.

The washed xylene phase is distilled under reduced pressure and concentrated (307.69 g of xylene). Subsequently, 148.08 g of methylcyclohexane are added and the mixture is cooled from ca. 78° C. to 23° C.

The suspension is filtered at 23-25° C. The moist filter cake is washed with methylcyclohexane and dried.

The yield is 90% of theory.

Example 2: One-Pot Method in DMAC (with Recycling after the DMAC Distillation) for Preparing the Compound of the Formula (I-1)

807.69 g of a solution of the compound of the formula (II-1) (0.81 mol) are initially charged in DMAC. At an internal temperature of 60-65° C., 159.04 g of a 30% sodium methoxide solution in methanol (0.88 mol) are metered in over ca. 2.5 h. Subsequently, methanol is distilled off under reduced pressure. The reaction solution is cooled to 50° C. and 9.62 g of triethylamine are metered in. Subsequently, 101.54 g of ethyl chloroformate (0.94 mol) are metered in between 52 and 56° C. over ca. 2.5 hours. The mixture is then further stirred for half an hour, then a portion of the DMAC is distilled off.

Subsequently, the residual DMAC is completely distilled off.

After addition of 403.85 g of xylene, the reactor content is cooled to 56° C.

Recycling: 3.85 g of triethylamine and 9.62 g of ethyl chloroformate (0.09 mol) are further metered in.

Subsequently, the xylene solution is heated to ca. 80° C. and 173.08 g of a 1.6% sodium hydrogen carbonate solution are added and the aqueous phase separated. Subsequently, the mixture is then washed twice with 107.69 g of water each time.

The washed xylene phase is distilled under reduced pressure and concentrated (307.69 g of xylene). Subsequently, 148.08 g of methylcyclohexane are added and the mixture is cooled from ca. 78° C. to 23° C.

The suspension is filtered at 23-25° C. The moist filter cake is washed with methylcyclohexane and dried.

The yield is 95% of theory.

Example 3: Preparation of the Compound of the Formula (I-1)

537.8 g of the compound of the formula (II-1) are initially charged in xylene/methanol (0.500 mol, ca. 31%). Methanol is distilled off at atmospheric pressure. 105 g of Na methoxide in methanol (0.583 mol, 30%) are metered in at 85° C.

over 1 h. During the metered addition of the Na methoxide, methanol is distilled off at 85° C. At the end of the metered addition, the mixture is stirred for 4 h at 85° C. In order to maintain the temperature of 85° C., methanol is distilled from time to time. After 4 h, the reaction is complete. The reaction mixture is cooled for the reaction to 80° C.

118.1 g of 2% HCl (0.06 mol) are initially charged at room temperature. To this charge, 437.8 g of the compound of the formula (III-1) in xylene/methanol (34%, 0.495 mol) are added. The mixture is subsequently distilled under reduced pressure until free of methanol. The mixture is cooled to 50° C. and 150 g of xylene and 15.3 g of triethylamine (0.150 mol) are added. Subsequently, 76.74 g of ethyl chloroacetate (0.700 mol, 99%) are metered in at 50° C. over 2 h. By means of parallel metering in of 32% aqueous sodium hydroxide solution, the pH is maintained between 9.5-10. The mixture is then stirred at 50° C. for 2 h. The pH is adjusted to 2 using an 18% hydrochloric acid solution and water is added. The mixture is heated to 75° C. for the phase separation, and the pH is readjusted with aqueous sodium hydroxide solution and subsequently the phases are separated. 150 g of 2% sodium hydrogen carbonate solution are added at 75° C. and the phases separated. The pH is ca. 8. The organic phase is dewatered and concentrated at ca. 75 mbar and 60-70° C. 90.6 g of methylcyclohexane are added at 75° C., whereupon solid (compound of the formula (I-1)) precipitates. The reaction mixture is heated to 109° C. (reflux), cooled to 20° C. and isolated. The solid (compound of the formula (I-1)) is washed by a displacement wash with MCH and subsequently dried. The isolated yield is 92-93% of theory based on the compound of the formula (II-1).

Example 4: Preparation of the Compound of the Formula (I-1)

537.8 g of the compound of the formula (II-1) are initially charged in xylene/methanol (0.500 mol, ca. 31%). Methanol is distilled off at atmospheric pressure. 105 g of Na methoxide in methanol (0.583 mol, 30%) are metered in at 85° C. over 1 h. During the metered addition of the Na methoxide, methanol is distilled off at 85° C. At the end of the metered addition, the mixture is stirred for 4 h at 85° C. In order to maintain the temperature of 85° C., methanol is distilled from time to time. After 4 h, the reaction is complete. The reaction mixture is cooled for the further reaction to 70° C.

To this mixture (compound of the formula (III-1) in xylene/methanol (34%, 0.495 mol)), 118.1 g of 2% HCl (0.06 mol) are added. The mixture is stirred for 15 min. at 70° C. and subsequently is distilled under reduced pressure at 350-250 mbar and 50-70° C. until free of methanol. The bottoms are biphasic. The mixture is cooled to 50° C. and 150 g of xylene and 15.3 g of triethylamine (0.150 mol) are added. Subsequently, 76.74 g of ethyl chloroacetate (0.700 mol, 99%) are metered in at 50° C. over 2 h. By means of parallel metering in of 32% aqueous sodium hydroxide solution, the pH is maintained between 9.5-10. The mixture is then stirred at 50° C. for ½ h. The pH is adjusted to 2 using an 18% hydrochloric acid solution and water is added. The mixture is heated to 75° C. for the phase separation, and the pH is readjusted with aqueous sodium hydroxide solution and subsequently the phases are separated. 150 g of 2% sodium hydrogen carbonate solution are added at 75° C. and the phases separated. The pH is ca. 8. The organic phase is dewatered and concentrated at ca. 75 mbar and 60-70° C. 90.6 g of methylcyclohexane are added at 75° C., whereupon solid (compound of the formula (I-1)) precipitates. The reaction mixture is heated to 109° C. (reflux), cooled to 20° C. and isolated. The solid (compound of the formula (I-1)) is washed by a displacement wash with MCH and subsequently dried.

The isolated yield is 96-98% of theory based on the compound of the formula (II-1).

Example 5: Preparation of the Compound of the Formula (I-1)

537.8 g of the compound of the formula (II-1) are initially charged in xylene/methanol (0.500 mol, ca. 31%). Methanol is distilled off at atmospheric pressure. 105 g of Na methoxide in methanol (0.583 mol, 30%) are metered in at 85° C. over 1 h. During the metered addition of the Na methoxide, methanol is distilled off at 85° C. At the end of the metered addition, the mixture is stirred for 4 h at 85° C. In order to maintain the temperature of 85° C., methanol is distilled from time to time. After 4 h, the reaction is complete. The reaction mixture is cooled for the further reaction to 80° C.

80 g of water are initially charged at room temperature. To this charge, 437.8 g of the compound of the formula (III-1) in xylene/methanol (34%, 0.495 mol) are added. The mixture is stirred for 15 min. at 70° C. and subsequently is distilled under reduced pressure at 350-250 mbar and 50-70° C. until free of methanol. The mixture is cooled to 50° C. and 150 g of xylene and 15.3 g of triethylamine (0.150 mol) are added. Subsequently, 76.74 g of ethyl chloroacetate (0.700 mol, 99%) are metered in at 50° C. over 2 h. By means of parallel metering in of 32% aqueous sodium hydroxide solution, the pH is maintained between 9.5-10. The mixture is then stirred at 50° C. for ½ h. The pH is adjusted to 2 using an 18% hydrochloric acid solution and water is added. The mixture is heated to 75° C. for the phase separation, and the pH is readjusted with aqueous sodium hydroxide solution and subsequently the phases are separated. 150 g of 2% sodium hydrogen carbonate solution are added at 75° C. and the phases separated. The pH is ca. 8.

The organic phase is dewatered and concentrated at ca. 75 mbar and 60-70° C. 90.6 g of methylcyclohexane are added at 75° C., whereupon solid (compound of the formula (I-1)) precipitates. The reaction mixture is heated to 109° C. (reflux), cooled to 20° C. and isolated. The solid (compound of the formula (I-1)) is washed by a displacement wash with MCH and subsequently dried.

The isolated yield is 96-98% of theory based on the compound of the formula (II-1).

Example 6: Preparation of the Compound of the Formula (I-1)

537.8 g of the compound of the formula (II-1) are initially charged in xylene/methanol (0.500 mol, ca. 31%). Methanol is distilled off at atmospheric pressure. 105 g of Na methoxide in methanol (0.583 mol, 30%) are metered in at 85° C. over 1 h. During the metered addition of the Na methoxide, methanol is distilled off at 85° C. At the end of the metered addition, the mixture is stirred for 4 h at 85° C. In order to maintain the temperature of 85° C., methanol is distilled from time to time. After 4 h, the reaction is complete. The reaction mixture is cooled for the further reaction to 80° C.

To this reaction mixture (437.8 g of the compound of the formula (III-1) in xylene/methanol (34%, 0.495 mol), 80 g of water are added (MeOH and NaCl is formed). The mixture is stirred for 15 min. at 70° C. and subsequently is distilled under reduced pressure at 350-250 mbar and 50-70° C. until free of methanol. The bottoms are biphasic. The mixture is cooled to 50° C. and 150 g of xylene and 15.3 g of triethylamine (0.150 mol) are added. Subsequently, 76.74 g of ethyl chloroacetate (0.700 mol, 99%) are metered in at 50° C. over 2 h. By means of the parallel metering in of 32% aqueous sodium hydroxide solution, the pH is maintained between 9.5-10. The mixture is then stirred at 50° C. for ½ h. The pH is adjusted to 2 using an 18% hydrochloric acid solution and water is added. The mixture is heated to 75° C. for the phase separation, and the pH is readjusted with aqueous sodium hydroxide solution and subsequently the phases are separated. 150 g of 2% sodium hydrogen carbonate solution are added at 75° C. and the phases separated. The pH is ca. 8.

The organic phase is dewatered and concentrated at ca. 75 mbar and 60-70° C. 90.6 g of methylcyclohexane are added at 75° C., whereupon solid (compound of the formula (I-1)) precipitates. The reaction mixture is heated to 109° C. (reflux), cooled to 20° C. and isolated. The solid (compound of the formula (I-1)) is washed by a displacement wash with MCH and subsequently dried.

Yield: 94% of theory based on the compound of the formula (II-1).

Example 7: Preparation of the Compound of the Formula (I-1)

537.8 g of the compound of the formula (II-1) are initially charged in xylene/methanol (0.500 mol, ca. 31%). Methanol is distilled off at atmospheric pressure. 20.69 g of Na methoxide in methanol (0.15 mol, 98%) are metered in at 85° C. over 1 h. During the metered addition, methanol is distilled off at 85° C. At the end of the metered addition, the mixture is stirred for 4 h at 85° C. In order to maintain the temperature of 85° C., methanol is distilled from time to time. After 4 h, the reaction is complete. The reaction mixture is cooled for the further reaction to 80° C. 118.1 g of 2% HCl (0.06 mol) are initially charged at room temperature. To this charge, 437.8 g of the compound of the formula (III-1) in xylene/methanol (34%, 0.495 mol) are added (MeOH and NaCl are formed). The mixture is stirred for 15 min. at 70° C. and subsequently is distilled under reduced pressure at 350-250 mbar and 50-70° C. until free of methanol. The mixture is cooled to 50° C. and 150 g of xylene and 20.69 g of dimethylbenzylamine (0.150 mol) are added. Subsequently, 76.74 g of ethyl chloroacetate (0.700 mol, 99%) are metered in at 50° C. over 2 h. By means of parallel metering in of 32% aqueous sodium hydroxide solution, the pH is maintained between 9.5-10. The mixture is then stirred at 50° C. for 2 h. The pH is adjusted to 2 using an 18% hydrochloric acid solution and water is added. The mixture is heated to 75° C. for the phase separation, and the pH is readjusted with aqueous sodium hydroxide solution and subsequently the phases are separated.

150 g of 2% sodium hydrogen carbonate solution are added at 75° C. and the phases separated. The pH is ca. 8. The organic phase is dewatered and concentrated at ca. 75 mbar and 60-70° C. 90.6 g of methylcyclohexane are added at 75° C., whereupon solid (compound of the formula (I)) precipitates. The reaction mixture is heated to 109° C. (reflux), cooled to 20° C. and isolated. The solid (compound of the formula (I-1)) is washed by a displacement wash with MCH and subsequently dried.

Yield: 83% of theory based on the compound of the formula (II-1).

Example 8: Preparation of the Compound of the Formula (I-1)

537.8 g of the compound of the formula (II-1) are initially charged in xylene/methanol (0.500 mol, ca. 31%). Methanol is distilled off at atmospheric pressure. 105 g of Na methoxide in methanol (0.583 mol, 30%) are metered in at 85° C. over 1 h. During the metered addition of the Na methoxide, methanol is distilled off at 85° C. At the end of the metered addition, the mixture is stirred for 4 h at 85° C. In order to maintain the temperature of 85° C., methanol is distilled from time to time. After 4 h, the reaction is complete. The reaction mixture is cooled for the reaction to 80° C. to give the active ingredient.

118.1 g of 2% HCl (0.06 mol) are initially charged at room temperature. To this charge, 437.8 g of the compound of the formula (III-1) in xylene/methanol (34%, 0.495 mol) are added. The mixture is stirred for 15 min. at 70° C. and subsequently is distilled under reduced pressure at 350-250 mbar and 50-70° C. until free of methanol. The mixture is cooled to 50° C. and 150 g of xylene and 15.3 g of triethylamine (0.150 mol) are added. Subsequently, 76.74 g of ethyl chloroacetate (0.700 mol, 99%) are metered in at 50° C. over 2 h. By means of parallel metering in of 32% aqueous sodium hydroxide solution, the pH is maintained between 9.5-10. The mixture is then stirred at 50° C. for ½ h. The pH is adjusted to 2 using an 18% hydrochloric acid solution and water is added. The mixture is heated to 75° C. for the phase separation, and the pH is readjusted with aqueous sodium hydroxide solution and subsequently phases are separated.

150 g of 2% sodium hydrogen carbonate solution are added at 75° C. and the phases separated. The pH is ca. 8.

The organic phase is dewatered at ca. 75 mbar and 60-70° C. The reaction mixture is heated to 109° C. (reflux), cooled to 0° C. and isolated. The solid (compound of the formula (I-1)) is washed by a displacement wash with xylene and subsequently dried.

Yield: 95% of theory based on the compound of the formula (II-1).

Example 9: Preparation of the Compound of the Formula (I-1)

537.8 g of the compound of the formula (II-1) are initially charged in xylene/methanol (0.500 mol, ca. 31%). Methanol is distilled off at atmospheric pressure. 105 g of Na methoxide in methanol (0.583 mol, 30%) are metered in at 85° C. over 1 h. During the metered addition of the Na methoxide, methanol is distilled off at 85° C. At the end of the metered addition, the mixture is stirred for 4 h at 85° C. In order to maintain the temperature of 85° C., methanol is distilled from time to time. After 4 h, the reaction is complete. The reaction mixture is cooled for the further reaction to 80° C.

118.1 g of 2% HCl (0.06 mol) are initially charged at room temperature. To this charge, 437.8 g of the compound of the formula (III-1) in xylene/methanol (34%, 0.495 mol) are added. The mixture is stirred for 15 min. at 70° C. and subsequently is distilled under reduced pressure at 350-250 mbar and 50-70° C. until free of methanol. The mixture is cooled to 50° C. and 150 g of xylene and 4.06 g of Aliquat 336 (0.01 mol) are added. Subsequently, 76.74 g of ethyl chloroacetate (0.700 mol, 99%) are metered in at 50° C. over 2 h. By means of parallel metering in of 32% aqueous sodium hydroxide solution, the pH is maintained between 9.5-10. The mixture is then stirred at 50° C. for ½ h. The pH is adjusted to 2 using an 18% hydrochloric acid solution and water is added. The mixture is heated to 75° C. for the phase separation, and the pH is readjusted with aqueous sodium hydroxide solution and subsequently the phases are separated.

150 g of 2% sodium hydrogen carbonate solution are added at 75° C. and the phases separated. The pH is ca. 8.

The organic phase is dewatered and concentrated at ca. 75 mbar and 60-70° C. 90.6 g of methylcyclohexane are added at 75° C., whereupon solid (compound of the formula (I-1)) precipitates. The reaction mixture is heated to 109° C. (reflux), cooled to 20° C. and isolated. The solid (compound of the formula (I-1)) is washed by a displacement wash with MCH and subsequently dried.

Yield: 85% of theory based on the compound of the formula (II-1).

Example 10: Preparation of the Compound of the Formula (I-1)

537.8 g of the compound of the formula (II-1) are initially charged in xylene/methanol (0.500 mol, ca. 31%). Methanol is distilled off at atmospheric pressure. 105 g of Na methoxide in methanol (0.583 mol, 30%) are metered in at 85° C. over 1 h. During the metered addition of the Na methoxide, methanol is distilled off at 85° C. At the end of the metered addition, the mixture is stirred for 4 h at 85° C. In order to maintain the temperature of 85° C., methanol is distilled from time to time. After 4 h, the reaction is complete. The reaction mixture is cooled for the further reaction to 80° C.

118.1 g of 2% HCl (0.06 mol) are initially charged at room temperature. To this charge, 437.8 g of the compound of the formula (III-1) in xylene/methanol (34%, 0.495 mol) are added. The mixture is stirred for 15 min. at 70° C. and subsequently is distilled under reduced pressure at 350-250 mbar and 50-70° C. until free of methanol. The mixture is cooled to 50° C. and 150 g of xylene, 6.12 g of triethylamine (0.150 mol) and 4.06 g of Aliquat 336 (0.01 mol) are added. Subsequently, 76.74 g of ethyl chloroacetate (0.700 mol, 99%) are metered in at 50° C. over 2 h. By means of parallel metering in of 32% aqueous sodium hydroxide solution, the pH is maintained between 9.5-10. The mixture is then stirred at 50° C. for ½ h. The pH is adjusted to 2 using an 18% hydrochloric acid solution and water is added. The mixture is heated to 75° C. for the phase separation, and the pH is readjusted with aqueous sodium hydroxide solution and subsequently the phases are separated.

150 g of 2% sodium hydrogen carbonate solution are added at 75° C. and the phases separated. The pH is ca. 8.

The organic phase is dewatered and concentrated at ca. 75 mbar and 60-70° C. 90.6 g of methylcyclohexane are added at 75° C., whereupon solid (compound of the formula (I-1)) precipitates. The reaction mixture is heated to 109° C. (reflux), cooled to 20° C. and isolated. The solid (compound of the formula (I-1)) is washed by a displacement wash with MCH and subsequently dried.

Yield: 86% of theory based on the compound of the formula (II-1).

Example 11: Preparation of the Compound of the Formula (I-1)

537.8 g of the compound of the formula (II-1) are initially charged in xylene/methanol (0.500 mol, ca. 31%). Methanol is distilled off at atmospheric pressure. 105 g of Na methoxide in methanol (0.583 mol, 30%) are metered in at 85° C. over 1 h. During the metered addition of the Na methoxide, methanol is distilled off at 85° C. At the end of the metered addition, the mixture is stirred for 4 h at 85° C. In order to maintain the temperature of 85° C., methanol is distilled from time to time. After 4 h, the reaction is complete. The reaction mixture is cooled to 60° C. and water is added. The phases are separated and the organic phase is discarded.

The aqueous enol phase is distilled under reduced pressure at 350-250 mbar and 50-70° C. until free of methanol. The mixture is cooled to 65° C., hydrochloric acid is added and solid sodium hydrogen carbonate is subsequently added. Into this mixture 67.11 g of ethyl chloroacetate (0.600 mol, 97%) are metered in at 65° C. over 2 h. The mixture is stirred at 75° C. for another 3 hours. A conversion (compound of the formula (I-1)) of 85% (HPLC) is determined.

Example 12: Preparation of the Compound of the Formula (I-1)

537.8 g of the compound of the formula (II-1) are initially charged in xylene/methanol (0.500 mol, ca. 31%). Methanol is distilled off at atmospheric pressure. 105 g of Na methoxide in methanol (0.583 mol, 30%) are metered in at 85° C. over 1 h. During the metered addition of the Na methoxide, methanol is distilled off at 85° C. At the end of the metered addition, the mixture is stirred for 4 h at 85° C. In order to maintain the temperature of 85° C., methanol is distilled from time to time. After 4 h, the reaction is complete. The reaction mixture is cooled to 60° C. and water is added. The phases are separated and the organic phase is discarded.

The aqueous enol phase is distilled under reduced pressure at 350-250 mbar and 50-70° C. until free of methanol. The mixture is cooled to 65° C., hydrochloric acid is added and solid sodium hydrogen carbonate is subsequently introduced. Into this mixture 10 g (0.098 mol) of triethylamine and 89.48 g of ethyl chloroacetate (0.800 mol, 97%) are metered in at 65° C. over 2 h. The mixture is stirred at 75° C. for another 3 hours. A conversion (compound of the formula (I-1)) of 75% (HPLC) is determined.

Example 13: Preparation of the Compound of the Formula (I-1)

537.8 g of the compound of the formula (II-1) are initially charged in xylene/methanol (0.500 mol, ca. 31%). Methanol is distilled off at atmospheric pressure. 105 g of Na methoxide in methanol (0.583 mol, 30%) are metered in at 85° C. over 1 h. During the metered addition of the Na methoxide, methanol is distilled off at 85° C. At the end of the metered addition, the mixture is stirred for 4 h at 85° C. In order to maintain the temperature of 85° C., methanol is distilled from time to time. After 4 h, the reaction is complete. The reaction mixture is cooled to 60° C. and water is added. The phases are separated and the organic phase is discarded.

The aqueous enol phase is distilled under reduced pressure at 350-250 mbar and 50-70° C. until free of methanol. The mixture is cooled to 55° C. and solid sodium hydrogen carbonate is introduced. Into this mixture 72.70 g of ethyl chloroacetate (0.650 mol, 97%) are metered in at 65° C. over 2 h. The mixture is stirred at 55° C. for another 3 hours and distilled until free of alcohol. 150 ml of xylene are added and the mixture is heated to 80° C. For the purpose of crystallization, the mixture is cooled to 20° C. and filtered. A conversion (compound of the formula (I-1)) of ca. 79% is determined by HPLC.

Comparative Example: Method for Preparing Compound of the Formula (I-1) with Intermediate Isolation of Compound of the Formula (III-1)

807.69 g of a solution of the compound of the formula (II-1) (0.81 mol) are initially charged in DMAC. At an internal temperature of 60-65° C., 159.04 g of a 30% sodium methoxide solution in methanol (0.88 mol) are metered in over ca. 2.5 h. Subsequently, methanol is distilled off under reduced pressure.

Subsequently, 440 g of water are added and the mixture is acidified at 60° C. with 60.3 g of conc. hydrochloric acid (37%) to pH 5.5. The precipitated solid is filtered off with suction at 20° C., washed twice with 130 g of water each time and dried under reduced pressure. Yield of 159.9 g of solid with a content of 98.0 g of compound (III-1) corresponding to a yield of 94.5%.

To a mixture of 500 g of methylcyclohexane, 28.4 g of triethylamine (98%) and 76.9 g of the compound of the formula (III-1) (98.0%), 30.4 g of ethyl chloroformate (98%) are metered in under boiling conditions over 15 min. After stirring for 4 h under reflux, the mixture is cooled to 80° C. and 180 g of water are added. The aqueous phase is removed with the dissolved triethylamine hydrochloride. Residual water is removed from the organic phase by azeotropic distillation and is cooled to 10° C. for complete crystallization of the active ingredient.

The precipitated solid is filtered off with suction, washed with 100 g of methylcyclohexane and dried under reduced pressure.

Yield: 88.6 g with a spirotetramat content of 98.8% (compound of the formula (I-1)) corresponding to a yield of 93.4%.

The yield over two stages based on the compound of the formula (II-1) is 88.3% of theory.

The invention claimed is:

1. A method for preparing a compound of formula (I)

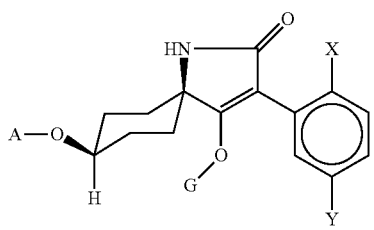

(I)

in which
X is $C_1$-$C_6$-alkyl, halogen, $C_1$-$C_6$-alkoxy, $C_1$-$C_6$-haloalkyl or $C_1$-$C_6$-haloalkoxy,
Y is hydrogen, $C_1$-$C_6$-alkyl, $C_1$-$C_6$-alkoxy, halogen, $C_1$-$C_6$-haloalkyl or $C_1$-$C_6$-haloalkoxy, wherein only one of the radicals X or Y may be $C_1$-$C_6$-haloalkyl or $C_1$-$C_6$-haloalkoxy,
A is $C_1$-$C_6$-alkyl,
G is the group

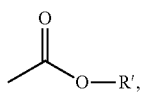

in which
R' is $C_1$-$C_{20}$-alkyl, $C_2$-$C_{20}$-alkenyl, $C_1$-$C_8$-alkoxy-$C_2$-$C_8$-alkyl or poly-$C_1$-$C_8$-alkoxy-$C_2$-$C_8$-alkyl, in each case optionally substituted by halogen,
is $C_3$-$C_8$-cycloalkyl optionally substituted by halogen, $C_1$-$C_6$-alkyl or $C_1$-$C_6$-alkoxy or
is phenyl or benzyl in each case optionally substituted by halogen, cyano, nitro, $C_1$-$C_6$-alkyl, $C_1$-$C_6$-alkoxy, $C_1$-$C_6$-haloalkyl or $C_1$-$C_6$-haloalkoxy, wherein firstly a compound of formula (II)

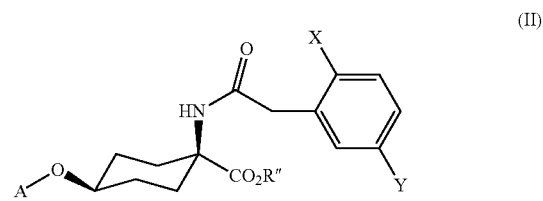

(II)

in which X, Y and A are as defined above and
R'' is $C_1$-$C_6$-alkyl,
are cyclized in the presence of a base and in the presence of one or more solvents to give compound of formula (III)

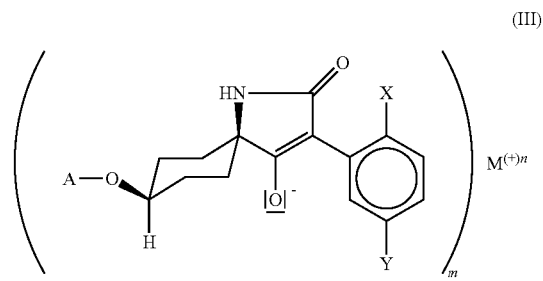

(III)

in which X, Y and A are as defined above and
M is an alkali metal ion, an ion equivalent of an alkaline earth metal, an ion equivalent of aluminium or an ion equivalent of a transition metal, or further
is an ammonium ion, in which optionally one, two, three or all four hydrogen atoms can be replaced by identical or different radicals from the groups $C_1$-$C_5$-alkyl, $C_1$-$C_5$-isoalkyl or $C_3$-$C_7$-cycloalkyl, which can in each case be substituted one or more times with fluorine, chlorine, bromine, cyano, hydroxy or be interrupted by one or more oxygen or sulphur atoms, or further
is a cyclic secondary or tertiary aliphatic or heteroaliphatic ammonium ion, or further
is a heterocyclic ammonium cation, or further
is a sulphonium ion, or further
is a magnesium halogen cation,
m is the number 1, 2 or 3,
n is the number 1, 2 or 3
and are reacted with a compound of formula (IV)

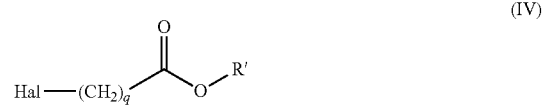

(IV)

in which
R' is $C_1$-$C_6$-alkyl,
q is the number 0 or 1,
and Hal represents halogen, optionally in the presence of one or more solvents and optionally in the presence of an acid binder and optionally in the presence of a phase transfer catalyst.

2. The method according to claim 1, wherein
X is chlorine, bromine, methyl, ethyl, propyl, trifluoromethyl, methoxy, difluoromethoxy or trifluoromethoxy,
Y is hydrogen, chlorine, bromine, methoxy, methyl, ethyl, propyl, trifluoromethyl or trifluoromethoxy, wherein only one of the radicals X or Y may be trifluoromethyl or trifluoromethoxy,
A is $C_1$-$C_6$-alkyl,
Hal is chlorine, bromine, fluorine or iodine,
R' is $C_1$-$C_6$-alkyl,
R" is $C_1$-$C_6$-alkyl,
q is the number 0 or 1.

3. The method according to claim 1, wherein
X is chlorine, bromine, methyl, ethyl, methoxy, trifluoromethyl, trifluoromethoxy or difluoromethoxy,
Y is chlorine, bromine, methyl, ethyl, propyl, methoxy, trifluoromethyl or trifluoromethoxy, wherein only one of the radicals X or Y may be trifluoromethyl or trifluoromethoxy,
A is $C_1$-$C_4$-alkyl,
Hal is chlorine, bromine or fluorine,
R' is $C_1$-$C_4$-alkyl,
R" is $C_1$-$C_4$-alkyl,
q is the number 0 or 1.

4. The method according to claim 1, wherein
X is chlorine, bromine, methyl or trifluoromethyl,
Y is chlorine, bromine or methyl,
A is methyl, ethyl, propyl, butyl or isobutyl,
Hal is chlorine or bromine,
R' is methyl, ethyl, propyl, butyl or isobutyl,
R" is methyl, ethyl, propyl, butyl or isobutyl,
q is the number 0 or 1.

5. The method according to claim 1, wherein
X is methyl,
Y is methyl,
A is methyl,
Hal is chlorine,
R' is methyl or ethyl,
R" is methyl or ethyl,
q is the number 0 or 1.

6. The method according to claim 1, wherein
X is methyl,
Y is methyl,
A is methyl,
Hal is chlorine,
R' is ethyl,
R" is methyl,
q is the number 0 or 1.

7. The method according to claim 1, wherein
M is lithium, sodium, potassium, caesium, magnesium, calcium or an ammonium ion, in which optionally one, two, three or all four hydrogen atoms can be replaced by identical or different radicals from the groups hydrogen, $C_1$-$C_5$-alkyl, $C_1$-$C_5$-isoalkyl or $C_3$-$C_7$-cycloalkyl, which can in each case be substituted one or more times with fluorine, chlorine, bromine, cyano, hydroxy,
m is the number 1 or 2 and n is the number 1 or 2.

8. The method according to claim 1, wherein
M is lithium, sodium, potassium, caesium, magnesium or calcium,
m is the number 1 or 2 and n is the number 1 or 2.

9. The method according to claim 1, wherein
M is lithium, sodium, potassium or caesium,
m is the number 1 and n is the number 1.

10. The method according to claim 1, wherein
M is sodium,
m is the number 1 and n is the number 1.

11. The method according to claim 1, wherein DMAC (dimethylacetamide) is used as solvent.

12. The method according to claim 1, wherein sodium methoxide is used as base.

13. The method according to claim 1, wherein triethylamine is used as acid binder.

14. The method according to claim 1, wherein dimethylbenzylamine is used as acid binder.

15. The method according to claim 1, wherein Aliquat 336 is used as phase transfer catalyst.

16. The method according to claim 1, wherein the compound of the formula (III) formed in a redissociation of compound of the formula (I), by reaction with compound of the formula (IV) optionally in the presence of a solvent and optionally in the presence of an acid binder, are recycled to give one or more compounds of the formula (I).

17. The method according to claim 1, wherein a non-polar solvent is used if the reaction of the compound of the formula (III) with a compound of the formula (IV) is carried out in the presence of water.

18. The method according to claim 17, wherein xylene is used as solvent.

19. The method according to claim 17, wherein methanol is used as cosolvent for the reaction of a compound of the formula (II) to give a compound of the formula (III).

20. The method according to claim 17, wherein sodium methoxide is used as base.

21. The method according to claim 17, wherein triethylamine is used as acid binder.

22. The method according to claim 17, wherein dimethylbenzylamine is used as acid binder.

23. The method according to claim 17, wherein Aliquat 336 is used as phase transfer catalyst.

24. The method according to claim 17, wherein aqueous sodium hydroxide solution is used as base to adjust the pH.

25. A compound of formula (III)

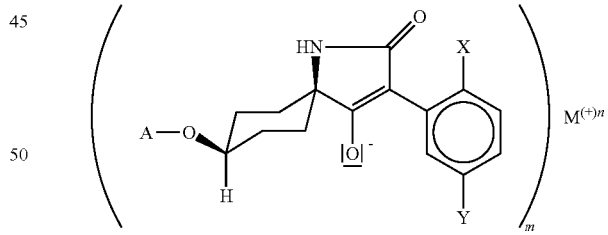

(III)

in which
X is $C_1$-$C_6$-alkyl, halogen, $C_1$-$C_6$-alkoxy, $C_1$-$C_6$-haloalkyl or $C_1$-$C_6$-haloalkoxy,
Y is hydrogen, $C_1$-$C_6$-alkyl, $C_1$-$C_6$-alkoxy, halogen, $C_1$-$C_6$-haloalkyl or $C_1$-$C_6$-haloalkoxy, wherein only one of the radicals X or Y may be $C_1$-$C_6$-haloalkyl or $C_1$-$C_6$-haloalkoxy,
A is $C_1$-$C_6$-alkyl,
M is an alkali metal ion, an ion equivalent of an alkaline earth metal, an ion equivalent of aluminium or an ion equivalent of a transition metal, or further is an ammonium ion, in which optionally one, two, three or all four hydrogen atoms can be replaced by identical or different radicals from the groups $C_1$-$C_5$-alkyl, $C_1$-$C_5$-isoalkyl or $C_3$-$C_7$-cycloalkyl, which can in each case be substituted one or more times with fluorine, chlorine, bromine, cyano, hydroxy or be interrupted by one or more oxygen or sulphur atoms, or further is a cyclic secondary or tertiary aliphatic or heteroaliphatic ammonium ion, or further is a heterocyclic ammonium cation, or further is a sulphonium ion, or further is a magnesium halogen cation, m is the number 1, 2 or 3, and n is the number 1, 2 or 3.

26. The method according to claim 1, wherein

M is an alkali metal ion, an ion equivalent of an alkaline earth metal, an ion equivalent of aluminium or an ion equivalent of a transition metal, or further is an ammonium ion, in which optionally one, two, three or all four hydrogen atoms can be replaced by identical or different radicals from the groups $C_1$-$C_5$-alkyl, $C_1$-$C_5$-isoalkyl or $C_3$-$C_7$-cycloalkyl, which can in each case be substituted one or more times with fluorine, chlorine, bromine, cyano, hydroxy or be interrupted by one or more oxygen or sulphur atoms, or further is morpholinium, thiomorpholinium, piperidinium, pyrrolidinium, or in each case protonated 1,4-diazabicyclo[2.2.2]octane (DABCO) or 1,5-diazabicyclo[4.3.0]undec-7-ene (DBU), or further is in each case protonated pyridine, 2-methylpyridine, 3-methylpyridine, 4-methylpyridine, 2,4-dimethylpyridine, 2,5-dimethylpyridine, 2,6-dimethylpyridine, 5-ethyl-2-methylpyridine, pyrrole, imidazole, quinoline, quinoxaline, 1,2-dimethylimidazole, 1,3-dimethylimidazolium methyl sulphate, or further is a sulphonium ion, or further is a magnesium halogen cation.

* * * * *